United States Patent [19]

Ryan

[11] Plant 4,259

[45] June 6, 1978

[54] IMPATIENS PLANT — NAVAJO

[76] Inventor: John J. Ryan, 39877 Sundale Dr., Fremont, Calif. 94538

[21] Appl. No.: 782,285

[22] Filed: Mar. 28, 1977

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Navajo, and discovered by me in commercial greenhouses in Fremont, Calif. Navajo is closest in characteristics to USDA Arabesque but is particularly characterized by rich red-green foliage with a very distinct golden brown to off-yellow variegation; a medium size, rose-red flower with a light eye; a very erect, thick, stiff stem; and very good breaking action, making an excellent pot and/or bedding plant.

2 Drawing Figures

BACKGROUND OF THE INVENTION

The present new variety (seedling 76-36-10) was discovered by me in a commercial greenhouse in Fremont, Calif. as a result of the cross pollination of unpatented pistil parent 75-15 and unpatented pollen parent 75-1.

Asexual reproduction of my new cultivar by terminal or stem cuttings grown in 6" pots in a plastic (polyethylene) greenhouse in Fremont, Calif. under normal environment conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Navajo is closest in characteristics to USDA Arabesque. The following outstanding characteristics of Navajo distinguish it from USDA Arabesque:

1. A rich red-green foliage with a very distinct golden brown to off-yellow variegation under high light, unlike the much lighter variegation of Arabesque.
2. A rose-red flower with a light eye and of medium size, unlike the large candy-striped flower of Arabesque.
3. Internode is short to medium; a very upright grower with a stiff, thick stem. Arabesque is not as stiff nor as upright.
4. Leaves do not cup down as much as Arabesque.

DESCRIPTION OF THE PHOTOGRAPH

The accompanying colored photograph illustrates the overall appearance of the cultivar Navajo showing the colors as true as reasonably possible for this type of colored reproduction. However, under high light the flower becomes a rose color and the variegation widens and becomes more distinct. Under low light the flower darkens and the variegation almost disappears; intensity of red leaf pigment decreases. The second photograph illustrates the leaf variability under different environmental conditions.

The following detailed description of NAVAJO is based on observations made of the new cultivar on Jan. 13, 1977.

PLANT

Name: Navajo.
Origin: Seedling 76-36-10 of the cross pollination of unpatented pistil parent 75-15 and unpatented pollen parent 75-1.
Form: Excellent upright.
Height to flower: — 38 cm.
Growth: Good.
Type of cutting: Terminal or stem.
Rooting time: Typical, 10–14 days.
Rooting habit: Fast, dendritic.

FOLIAGE

Arrangement: Lower leaves opposite (usually only one set); upper foliage on a break, whorled 3–6.
Shape: Elliptic to oblanceolate.
Tip: Acuminate.
Base: Attenuate.
Margin: Ciliate at base to serrulate at tip.
Venation: Pinnate.
Size: Petiole and blade 17.5 cm., length of blade 14.5 cm., width of blade at widest point 4.5 cm.
Surface: Glabrous, waxy
Variegation: Increases with age of plant and light intensity.
Color:
*Petiole.*—Upper 185C, lower 185A.
*Veins.*—185A.
*Leaf.*—a. Upper: mature upper 147A, mature lower 136B. b. Lower: 138B with red sheen.
*Variegation:*

| | | |
|---|---|---|
| a. *Edge: 147A* | | |
| b. Middle: 136A | } | Blending |
| c. Center: 137C | | |

STEM

Color: 47B at top of plant, fading out as one approaches the bottom.
Internode:
*Length.*—Moderate.
*Size.*—Heavy.

Node expanded (relative to internode): Moderate expansion.

Breaking action: Moderate to good for a pot variety.

FLOWER

Form: Typical.

Borne: End of braches, terminal.

Blooming habit:

*Relative number.*—Moderate.

*Time in flowering.*—Moderate.

*Longevity.*—5 days, heavily dependent on temperature.

Size:

*Length.*—6 cm.

*Width.*—5.5 cm.

*Spur.*—5 cm.

Color:

*Eye:*

| | |
|---|---|
| 1. *Eye: Bluish red 50B fading to white 49C* | |
| 2. Middle | 43 C |
| 3. Edge | |
| 4. Pedicel: 52 C | |

*Pedicel.*—52 C.

REPRODUCTIVE ORGANS

Stamen:

| | |
|---|---|
| 1. Anthers | typical in form, fused hood over pistil |
| 2. Filament | |
| 3. Pollen: | |
| a. Color: 160C | |
| b. Abundance: Typical, plenty | |

Pistils:

| | |
|---|---|
| 1. Style | typical in form |
| 2. Ovaries | |

OTHER CHARACTERISTICS

Diseases: Navajo is less susceptible than other varieties to most soft rots.

I claim:

1. A new and distinct form of Impatiens plant as described and illustrated known by the cultivar name Navajo and particularly characterized by rich red-green foliage with a very distinct golden brown to off-yellow variegation; a medium size, rose-red flower with a light eye; a very erect, thick, stiff stem; and very good breaking action, making an excellent pot and/or bedding plant.

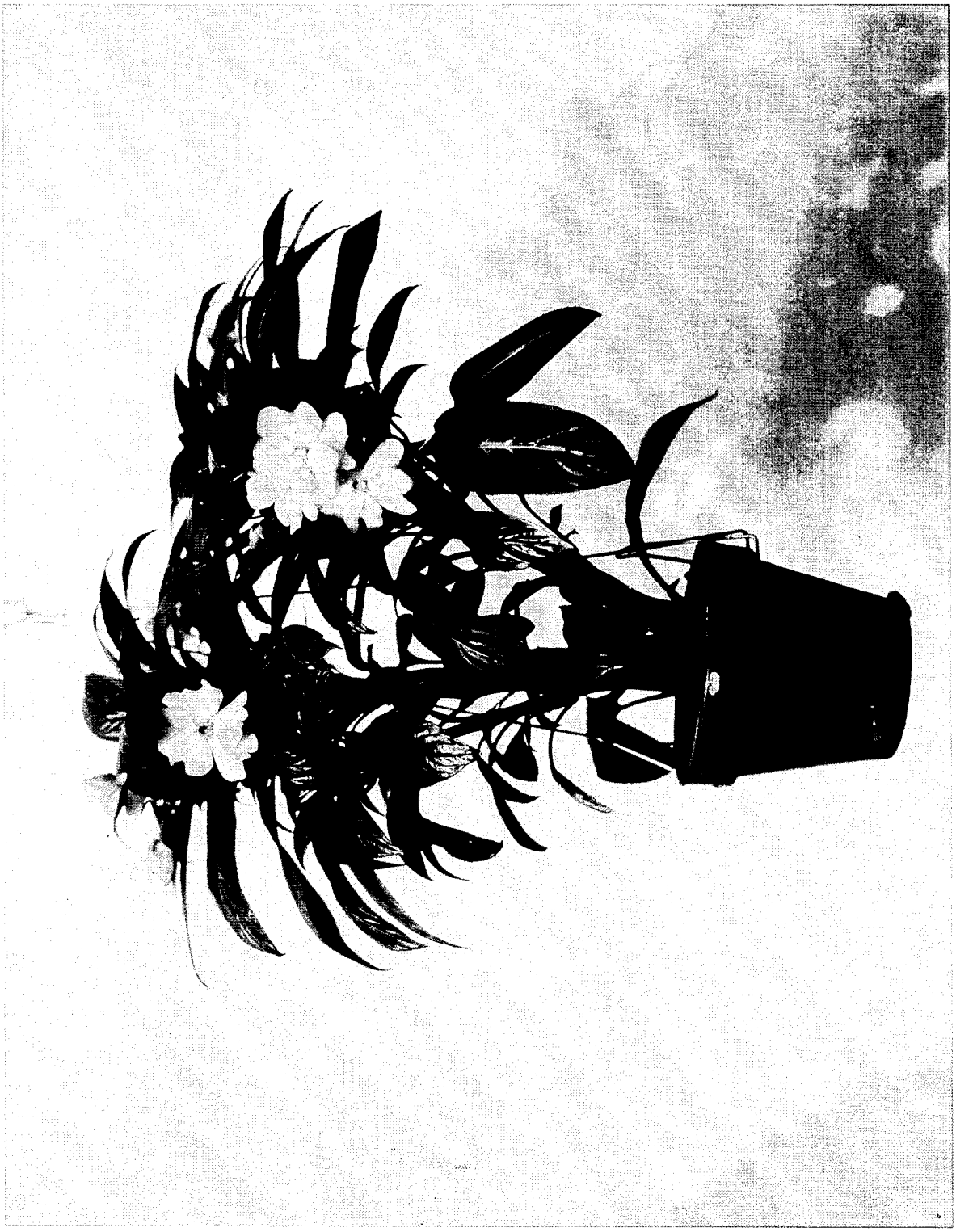

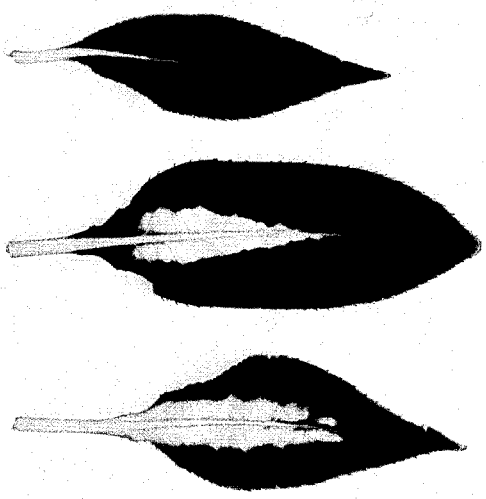

* * * * *